United States Patent [19]
Nakajima et al.

[11] Patent Number: 5,688,686
[45] Date of Patent: Nov. 18, 1997

[54] FERMENTATION APPARATUS

[76] Inventors: Shigeji Nakajima, 7-6, Sengoku-cho 4-chome, Hitachi-shi, Ibaraki-ken; Teruo Nakamura, 187-155, Nozawa-cho, Utsunomiya-shi, Tochigi-ken; Shigeru Sato, 30-7, Kuwamizu 1-chome, Kumamoto-shi, Kumamoto-ken, all of Japan

[21] Appl. No.: 552,525

[22] Filed: Nov. 6, 1995

[30] Foreign Application Priority Data

Mar. 22, 1995 [JP] Japan ................................ 7-63174

[51] Int. Cl.⁶ ................................................ C05F 17/02
[52] U.S. Cl. .................................. 435/290.2; 435/290.4; 366/297; 366/325.1; 366/345
[58] Field of Search ........................... 435/290.2, 290.4, 435/294.1; 71/9; 366/297, 298, 331, 345, 346, 325.1, 281, 283, 292

[56] References Cited

U.S. PATENT DOCUMENTS

| | | | |
|---|---|---|---|
| 2,734,803 | 2/1956 | Ruskin | 71/9 |
| 3,114,622 | 12/1963 | Hardy | 71/9 |
| 3,357,812 | 12/1967 | Snell | 71/9 |
| 4,148,590 | 4/1979 | Sotirianos | |
| 4,193,786 | 3/1980 | Brill | |

FOREIGN PATENT DOCUMENTS

| | | | |
|---|---|---|---|
| 3829018 | 3/1990 | Germany | 71/9 |
| 57-149889 | 9/1982 | Japan | 71/9 |
| 59-111991 | 6/1984 | Japan | 435/290.2 |
| 90/00162 | 1/1990 | WIPO | 435/290.2 |

*Primary Examiner*—William H. Beisner
*Attorney, Agent, or Firm*—Tarolli, Sundheim, Covell, Tummino & Szabo

[57] ABSTRACT

The fermentation apparatus according to the invention is of a vertically oriented, multistage type comprising one or more fermentation tanks, an outlet port provided at the top of the fermentation tank, a maturation tank disposed below the fermentation tank, and a preliminary fermentation tank disposed below the maturation tank. Each fermentation tank includes a support member rotatable in the circumferential direction, an agitation member removably connected to the support member and including a plurality of agitation blades rotatable in the horizontal direction relative to the bottom surface of the fermentation apparatus, a gas intake device disposed below the agitation member, a transfer opening member for open-close movement, and a filter member provided at the top of the fermentation tank.

6 Claims, 6 Drawing Sheets

FERMENTATION APPARATUS

BACKGROUND OF THE INVENTION

1. Filed of the Invention

This invention relates to a vertically oriented, multistage, multi-purpose fermentation apparatus. More particularly, the invention relates to a vertically oriented, multistage, multi-purpose fermentation apparatus useful in composing organic sludge and de-watered sludge from excrement, food residue, organic waste such as garbage, and organic waste liquid, for the purpose of regenerating them as a fertilizer.

2. Prior Art

Generally, organic sludge from excrement, for example, has a high water content equal to or more than 95%. Several methods have been proposed for composing organic sludge or the like having a high water content. In one method, solid-liquid separation is performed on the output from an activated sludge process for a subsequent fermentation process. In another method, and in place of performing the solid-liquid separation, a quantity of sawdust is put into the output from an activated sludge process in order to regulate the water content for a subsequent fermentation process. It is noted, however, that, in the activated sludge process in which only the liquid is treated, nitrogen, phosphoric acid and the like are not sufficiently treated. The activated sludge process also requires a high cost for treatment installation. On the other hand, and in the method in which sawdust is used for moisture conditioning purpose, it is necessary to complete compost the sludge, as well as the sawdust used as a moisture conditioner. Since sawdust includes a large quantity of persistent substances, such as lignin, which are difficult to be treated, the volume of sawdust to be used is limited.

A sludge composing process employing a conventional composing apparatus was disadvantageous in that it requires a long treatment time, usually about a half year, and a large area of land for installation of the treatment equipment. Such a process is also disadvantageous in terms of the treatment of odor and effluent from the treatment equipment, and its high running cost.

In order to solve the above problems, a method was proposed in which sludge sediment under treatment is "turned-over" and splashed so as to increase the possibility of contact thereof with air for increasing the activity of aerophilic bacteria, whereby the occurrence of putrefactive odor derived from aerophobic bacteria is restricted. It is noted, however, that, when the contact area between the sludge sediment under treatment and air is increased, the sludge sediment is easily cooled by air, so that the activity of microorganisms in the sludge sediment is reduced. Thus, the above method in which the sludge sediment is "turned-over" decreases not only the activity of aerophobic bacteria by increasing the contact area between the sludge sediment and air, but also the activity of aerophilic bacteria by decreasing the temperature of the sludge sediment, so that it is difficult for such a method to increase fermentation efficiency. Although it is conceivable to maintain the sludge sediment at an appropriate temperature by using an external heat source, this causes the apparatus to be complex. It also causes the running cost of the apparatus to be higher. Such an external heat source also decreases the water content of the sludge sediment due to evaporation phenomenon, so that growth of microorganisms is attenuated. This causes a significant problem in that the sludge sediment is matured insufficiently, so that improperly formed compost is produced.

In spite of the above-mentioned several efforts, prior art composing apparatuses failed to achieve sufficient composing of sludge sediment. Thus, the compost obtained according to prior art apparatuses not only contains a residual odor, but also causes re-fermentation of micro-organisms in the compost, of which activity has been attenuated due to insufficient moisture content, as a result of an increase in the environmental temperature when the compost is applied to soil. In this way, nitrogen in the soil is disadvantageously absorbed in the compost, so as to cause a problem of "nitrogen deficiency".

It is also noted that, according to prior art composing processes of sludge sediment, the sludge sediment should be stored for a certain period of time to enable fermentation and maturation thereof. This also invites some problems in that odor results from the growth of aerophobic bacteria during a composing process, and that effluent derived from the sludge sediment is required to be treated. Occurrence of such an odor and effluent is particularly problematic in view of urbanisation whereby a treatment installation may be located on an area adjacent a residential section.

With regard to a composing process for organic waste such as food residue and garbage, and organic effluent, a conventional method has been used in which such organic waste etc. is fermented for decomposition thereof by means of aerophobic bacteria in soil. Such method utilizing self-purifying function of the soil is suitable for the treatment of a small amount of organic waste, but is not suitable for the treatment of a large amount of organic waste. The method is also problematic in view of the odor inherent in the organic waste and odor caused by aerophobic bacteria during the fermentation process.

The generation of offensive odors is a serious problem with respect to not only the treatment of miscellaneous household effluent, but also with regard to the food processing industry for animal meat, fish meat etc. In such industry, waste water is directly discharged to a river or sea without performing any treatment.

SUMMARY OF THE INVENTION

It is therefore an object of the invention to provide a vertically oriented, multistage, multi-purpose fermentation apparatus which is capable of eliminating the above problems experienced in prior art. Specifically, the object of the invention is to provide a vertically oriented, multistage, multi-purpose fermentation apparatus which may:

(1) facilitate effective land use;

(2) restrict occurrence of odorous gas during a fermentation process by performing compulsive supply and exhaust of air so as to always maintain the environment within the apparatus at a constant pressure;

(3) restrict occurrence of odorous gas by increasing the activity of microorganisms mainly consisting of aerophilic bacteria so as to increase fermentation efficiency, while restricting the activity of aerophobic bacteria;

(4) increase fermentation efficiency, by utilizing the heat caused from biochemical, exothermic reaction to the greatest possible extent, without using any external heat source, so as to maintain the temperature of the sludge sediment at an optimum value;

(5) restrict the occurrence of effluent produced in prior arts, by evaporating water in the sludge using the heat from exothermic, biochemical reaction;

(6) reasonably activate the biochemical reaction by providing environment optimal to the change or transition of microorganisms; and (7) provide the apparatus with universality in terms of kinds or sorts and capacity of treatment of organic waste to be treated.

One of the inventors of this application proposed a "method of composing excrement" (Japanese Patent No. 1829732). According to the patented method, organic material is preliminarily fermented. The product from the preliminary fermentation is mixed with a quantity of dry material, such as sawdust, having a water content of less than 15 wt %, so as to achieve a C/N ratio (carbon to nitrogen ratio) of 25 to 30 wt %. The resultant mixture is mixed with a quantity of excrement at a ratio of 30 to 40 wt % relative to the total weight of the excrement. By this means, the excrement in a liquid phase is transformed into a gel phase, so as to permit air to penetrate into the inside of the solid. The mixture is then fermented under the presence of oxygen at a high temperature of 65 to 70 degrees Celsius and transferred into the maturation tank so as to be further fermented under the presence of oxygen at a medium temperature of 35 to 40 degrees Celsius.

The vertically oriented, multistage, multi-purpose fermentation apparatus of the invention is particularly suited to making use of a small land area, and to efficiently perform the above composing process.

In general, the vertically oriented, multistage, multi-purpose fermentation apparatus according to the invention comprises: at least one fermentation tank including a housing of a substantially cylindrical configuration; a support means extending radially outwardly from the center of the fermentation tank and being rotatable about the center of the fermentation tank; a plurality of agitation means removably connected to and supported by the support means, each of the agitation means including a plurality of agitation blades each of which is rotatable about its rotary axis extending vertically to the bottom surface of the fermentation tank; a gas intake means disposed above the bottom surface of the fermentation tank and below the agitation means; a transfer opening means disposed in the bottom surface of the fermentation tank and arranged to be opened and closed; at least one filter means disposed in the top surface of the fermentation tank at the uppermost stage; and a maturation tank disposed below the fermentation tank at the lowermost stage and being in communication with the fermentation tank through the transfer opening means.

It is to be noted that, it is possible for the sediment to be agitated without causing splashing by means of the agitation means, referred to as a "stand impeller" system by the inventors, including a plurality of agitation blades rotatable in a plane substantially in parallel with the bottom surface of the agitation tank. In addition, it is also possible to supply a quantity of gas such as air necessary for the activation of aerophilic bacteria into the inside of the sediment from the bottom thereof, by using the gas intake means disposed below the agitation means. Thus, it is possible to satisfy at the same time the above contradictive subjects of (3) to restrict occurrence of odor gas by increasing the activity of microorganisms mainly consisting of aerophilic bacteria so as to increase fermentation efficiency, while restricting the activity of aerophobic bacteria and (4) to increase fermentation efficiency, by utilizing the heat caused from biochemical, exothermic reaction to the greatest possible extent, without using any external heat source, so as to maintain the temperature of the sludge sediment at an optimum value.

Preferably, the apparatus includes at least two fermentation tanks disposed above the maturation tank and connected with each other. In this case, the fermentation tank at the upper stage functions as a high-temperature fermentation tank (65 to 70 degrees Celsius) for thermophilic bacteria, and the fermentation tank at the lower stage functions as a medium-temperature fermentation tank (30 to 40 degrees Celsius) for methophilic bacteria. The maturation tank serves as a low-temperature fermentation tank (room temperature) for cryophilic bacteria.

Preferably, the filter means includes as a deodorizing filter medium microorganisms changed from thermophilic bacteria to methophilic bacteria. The microorganisms present in a compost having been matured in accordance with the composing process disclosed in the above-mentioned Japanese Patent No. 1829732. In practice, such compost may be used as deodorizing filter media. The above microorganisms contain therein, as an odor source, microorganisms for causing oxidization and decomposition of ammonia, methyl mercaptan, hydrogen sulfide, methyl sulfide and the like, protozoans such as sulfur bacteria, bacteria such as bacillus, comma bacillus, methane bacteria, filamentous bacteria, fungi such as yeast. The use of such compost containing the above microorganisms as a deodorizing filter media facilitates natural selection of microorganisms in accordance with their respective habitat environment, such as the total amount, concentration, and the kinds of the odor causing gases. Thus, particular kinds of micro-organisms most effective for deodorization are successively grown in the compost to form an appropriate filter bed.

The filter means is disposed in the top surface of the fermentation tank at the uppermost stage, so as to deodorize the gas caused within the fermentation tanks. It is noted, however, that the filter means may be provided at each of the fermentation tanks, so as to increase deodorizing effect of the apparatus. When the filter means is provided at each of the fermentation tanks, it is preferable to transfer the gas having been deodorized at each fermentation tank to the filter means provided at the fermentation tank at the uppermost stage through the gas transfer means, for the purpose of further deodorization treatment. It is also preferable for the filter means at each fermentation tank to include a particular filter bed containing optimal kinds of microorganisms depending upon the constituents and concentration of a given odor gas.

Preferably, the fermentation tank includes a cylindrical housing in order to facilitate sufficient and uniform fermentation reaction throughout the fermentation tank, the cylindrical housing having on its central axis of a supporting point for the above support means. The support means includes at least one arm extending radially from the supporting point toward the side wall (peripheral wall) of the fermentation tank. Preferably, the support means includes a pair of arms oppositely disposed with respect to the supporting point. The agitation means is disposed below the arm(s).

The agitation means includes a drive shaft on which the plurality of agitation blades are carried. The drive shaft for the agitation blades is removably connected to the arm and extends downwardly from the arm in the vertical direction. The drive shaft for the agitation blades is rotatable independently of the rotation of the arm. Since the drive shaft for the agitation blades is removably connected to the arm, it is possible to provide a plurality of drive shafts carrying thereon agitation blades of a different size attached to the drive shaft at different angles. Thus, agitation conditions may be easily changed depending upon the kind of sediment to be treated.

The support means in each of the fermentation tanks may be adjustably controlled, so as to obtain speed and direction of rotation thereof most suitable for a particular fermentation condition within each fermentation tank.

Further, the speed and direction of rotation of the agitation means in each of the fermentation tanks may be adjustably controlled. It is also noted that the plurality of agitation blades may be adjustably and independently controlled with respect to their speed and direction of rotation so as to obtain substantially uniform fermentation conditions in each of the fermentation tanks, whereby uneven progress of fermentation throughout each fermentation tank (for example, better fermentation is obtained in the central portion of the fermentation tank, while less fermentation is obtained in the area adjacent to the side wall thereof) may be prevented.

In order to regulate rotation of the support means, agitation means and agitation blades, it is also possible to provide a sensing means which senses the progress of fermentation of sediment in the fermentation tank.

The gas intake means is provided at a position above the bottom surface of the fermentation tank and below the agitation means. Preferably, the gas intake means includes a plurality of tubular members having air supply openings (air diffusion pipes or perforated pipes). It is also preferable that each tubular member includes a main body, a head and a shoulder, the shoulder having the above air supply openings. In such a case, a flow of gas from the air supply openings is once ejected toward the bottom surface of the fermentation tank and then directed upwardly, so that it is uniformly diffused throughout the sediment. The tubular members are sized so as to obtain a maximum volume of gas supply depending upon a particular quantity of sediment to be treated. It is also possible to provide a means for regulating a quantity of air supply at an appropriate rate.

In order to transfer the sediment in each of the fermentation tanks to the next stage of fermentation tank or maturation tank, after completion of fermentation process therein, the transfer opening means is provided in the bottom surface of the fermentation tank. The transfer opening means may be in the form of a conventional dumper. Thus, the bottom surface of the fermentation tank may be designed to be opened downwardly. The open-close operation of the transfer opening means may be controlled automatically according to a predetermined time schedule or treatment condition. Alternatively, the open-close operation of the transfer opening means may be manually controlled depending upon a given treatment condition.

The maturation tank is disposed below the fermentation tank at the lowermost stage and communicated with the fermentation tank through the transfer opening means. Within the maturation tank, the sediment is matured by reason of biochemical reaction of methophilic bacteria and/ or cryophilic bacteria. The maturation tank may be provided with an area for storing a quantity of moisture conditioner, a pre-heating area, an area for storing the sediment having been fermented, and an outlet port for discharging the sediment stored therein.

Preferably, a liquid fermentation tank is disposed below the maturation tank, the liquid fermentation tank serving as a preliminary fermentation tank. The liquid fermentation tank preferably includes a diffuser and a liquid transfer means such as a transfer pump, so as to transfer a quantity of liquid after preliminary fermentation into the fermentation tank.

The vertically oriented, multistage, multi-purpose fermentation apparatus provides the following advantages:

(1) Since the apparatus is of a multistage type in the vertical direction, effective land use is permitted. Provision of the liquid fermentation tank at the lowermost stage as a preliminary fermentation tank permits all fermentation processes to be performed within the apparatus. This further contributes to effective land use.

(2) Odor gas and effluent caused during fermentation process are not discharged out of the apparatus. A compost on which microorganisms are fixed is used as a deodorizing filter medium, so that optimal deodorizing effect may be obtained.

(3) The gas intake means is provided in the bottom surface of each of the fermentation tanks. Further, the agitation blades, referred to as a "stand impeller" type, are rotated in a horizontal plane. This facilitates activity of aerophilic bacteria so as to increase fermentation efficiency, while restricting activity of aerophobic bacteria so as to reduce the occurrence of odor.

(4) The use of agitation blades of a "stand impeller" type rotating in a horizontal plane prevents "turn-over" of the sediment, so that heat diffusion is restricted. Thus, it is possible to maintain the sludge sediment at an appropriate temperature, without using any external heat source, so as to facilitate activity of microorganisms and to increase fermentation efficiency.

(5) Different types of drive shafts to which agitation blades of a different size and a different angle are attached may be interchangeably used. This provides the apparatus of the invention with universability in terms of kinds and volume of organic waste to be treated.

DETAILED DESCRIPTION OF THE PREFERRED EMBODIMENTS

The invention will be explained in detail below with reference to the attached drawings. It should be understood, however, that the invention is not limited to the illustrated embodiments.

Figure 1:
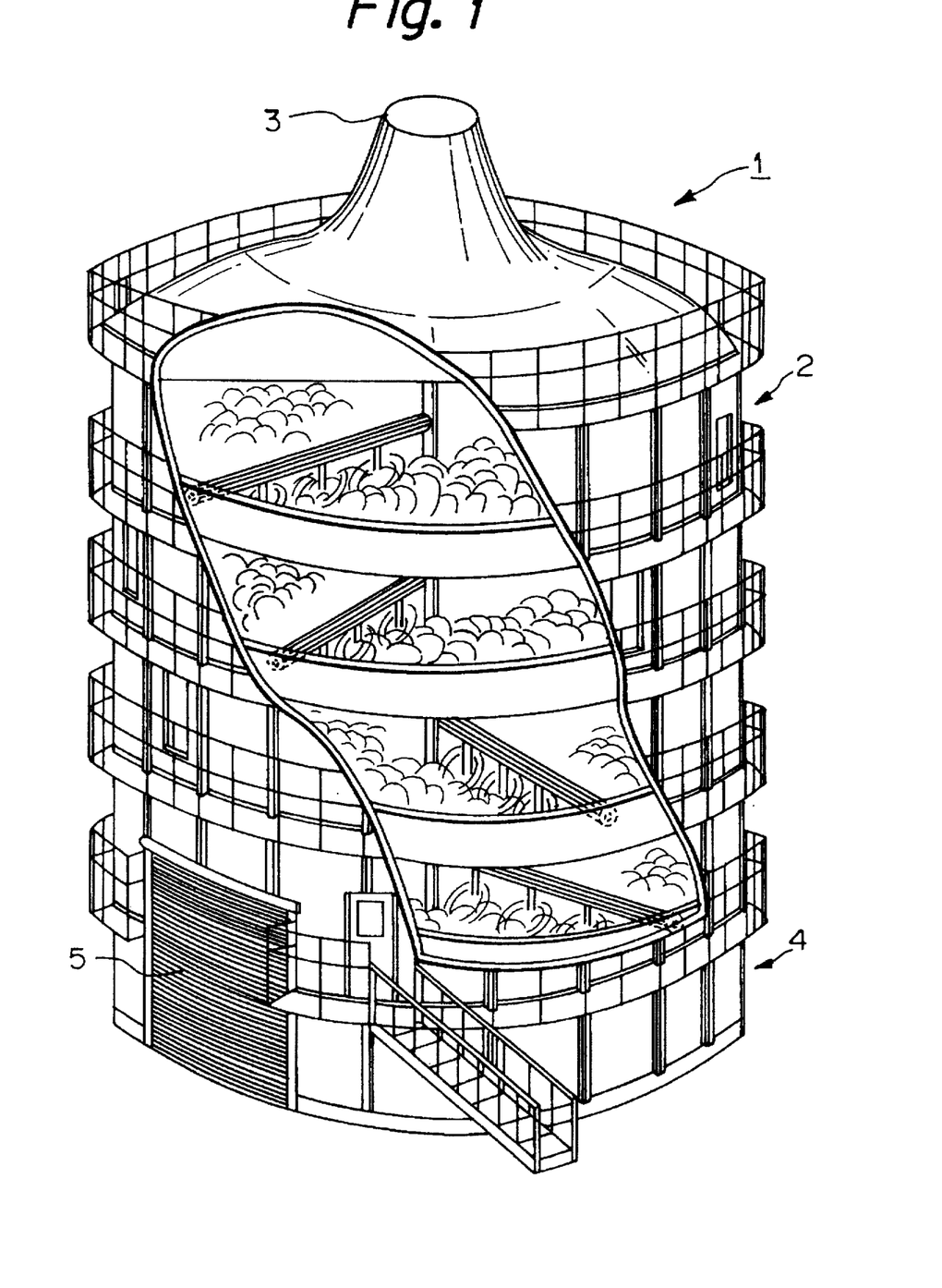
FIG. 1 is a diagrammatic, perspective view illustrating a vertically oriented, multistage, multi-purpose fermentation apparatus according to the invention.
Figure 2:
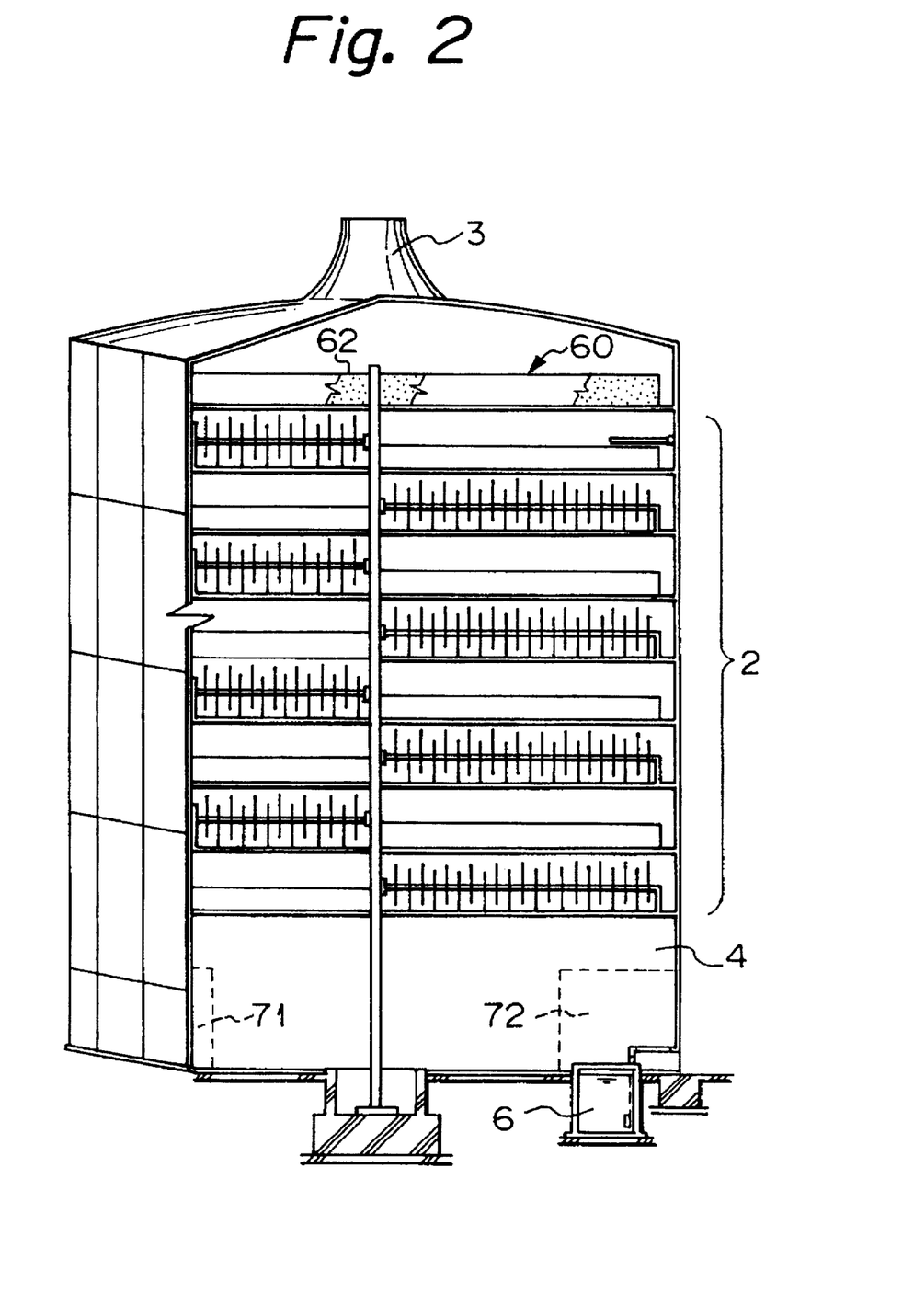
FIG. 2 is a vertical cross-sectional view of the vertically oriented, multistage, multi-purpose fermentation apparatus according to the invention.

FIG. 1 is a perspective view illustrating an outline of a vertically oriented, multistage, multi-purpose fermentation apparatus, and FIG. 2 is a cross-sectional view of the vertically oriented, multistage, multi-purpose fermentation tank. The vertically oriented, multistage, multi-purpose fermentation tank 1 of a cylindrical configuration in its entirety comprises multiple stages of fermenters or fermentation tanks 2, a gas outlet port 3 provided at the top of the uppermost fermentation tank 2, a maturation tank 4 located at the bottom of the fermentation apparatus, an output port 5 for removing compost (compost output port) provided at the side wall of the maturation tank, and a fermentation tank 6 for liquid (liquid fermentation tank). In FIG. 2, a vertically oriented, multistage, multi-purpose fermentation apparatus consisting of 8 stages of fermentation tanks 2 according to one embodiment of the invention is illustrated. In the 8 stages of fermentation tanks, the upper 4 stages of fermentation tanks function as a high-temperature tank and the lower 4 stages of fermentation tanks function as an intermediate-temperature tank. The maturation tank 4 functions as a low-temperature tank. The sediment having been fermented within the fermentation tank 2 is further matured in the maturation tank 4 and stored therein. A deodorization device 60 is provided at the top of the uppermost-stage fermentation tank 2. Thus, odor produced during fermentation treatment is removed from an exhaust gas before the exhaust gas is discharged from the gas outlet port 3.

Figures 3A, 3B:
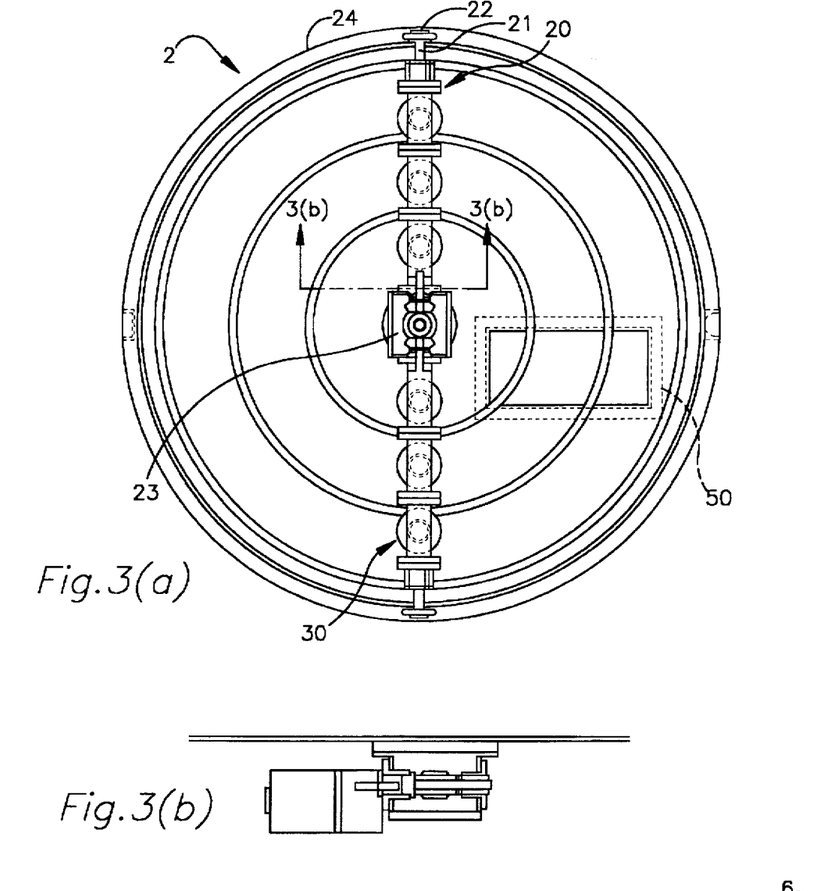
FIG. 3(a) is a top plan view of a fermenter or fermentation tank.
FIG. 3(b) is a cross-sectional view along line B—B of FIG. 3(a)
Figure 4:
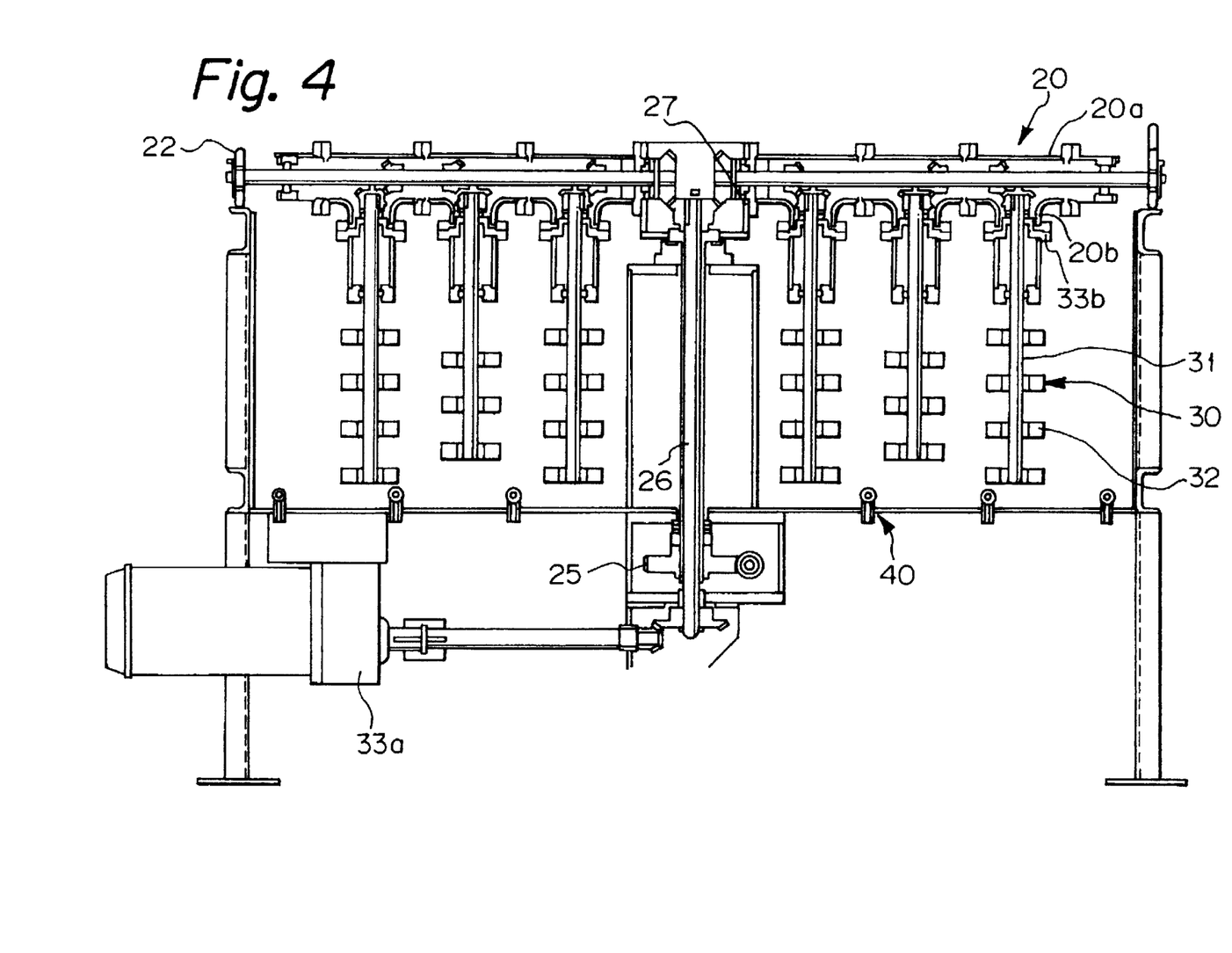
FIG. 4 is a cross-sectional view of the fermenter of FIG. 3.

FIG. 3 is a plan view illustrating the internal construction of each of the fermentation tank 2, and FIG. 4 is a vertical cross-sectional view along the center line of the fermentation tanks.

Each fermentation tank 2 includes a support means 20 having two arms extending radially outward from the center of the fermentation tank toward the opposed sides thereof, a first drive means 23 for rotationally driving the support means 20, a plurality of agitation means 30 connected with and supported by the support means 20, a plurality of agitation blades 32 mounted on each agitation means 30, a second drive means 33 for rotationally driving the plurality of agitation means 30, a plurality of gas intake means 40 disposed in the bottom surface of the fermentation tank 2 at the positions below the plurality of agitation means 30, and a transfer opening means 50 arranged in the bottom surface for open-close movement.

The support means 20 includes a hollow, cylindrical body 20a and connection parts 20b protruding downwardly from the underside of the hollow, cylindrical body 20a. Within the hollow, cylindrical body 20a, two support arms 21 are also provided which extend radially outward from the center of the fermentation tank toward the opposed sides thereof. Each support arm 21 is connected, at its end facing to the center of the fermentation tank, to the first drive means 23 through a conventional joint. On the other hand, the peripheral end of each of the arms is provided with a guide wheel 22. The guide wheel 22 is received by a guide rail 24 provided in the peripheral wall of the fermentation tank 22 and guided thereby.

As shown in FIG. 4, the first drive means 23 is adapted to transmit driving force from a motor (not shown) to an outer drive shaft 26 through a worm gear 25, and then to rotatably drive the support arm 21 through a pair of bevel gears 27 disposed on the opposite sides of the drive shaft 26 at the portion where the drive shaft 26 is connected to the support arms 21.

The agitation means 30 includes a plurality of drive shafts 31. Each drive shaft 31 is provided with a plurality of agitation blades 32. The agitation blades 32 are attached to the corresponding drive shafts for rotation about the vertical axis thereof in a plane substantially horizontal to the bottom surface of the fermentation tank 2. Each drive shaft 31 for the agitation blades 32 includes one end inserted into the connection part 20b of the first support means 20 so as to form the first support means and the other end extending vertically toward the bottom surface of the fermentation tank 2. Each drive shaft 31 for the agitation blades 32 is removably connected to the first support means 20, so as to permit one to use various kinds of agitation blades depending upon a particular type of sediment or sludge to be treated by means of fermentation process.

The agitation means 30 is rotatably driven by means of the second drive means 33. Driving force from the motor 33a is transmitted, through the inside of the drive shaft 26, and through the support arm 21, to bevel gears 33b provided at each connection part 20b between the support arm 21 and the drive shafts 31 for the agitation blades 32, whereby the drive shafts 31 for the agitation blades 32 are rotatably driven by the respective bevel gears 33b. Alternatively, it is also possible to mount a motor on each connection part 20b, so that each drive shaft 31 for the agitation blades 32 is individually rotated.

Figure 5:
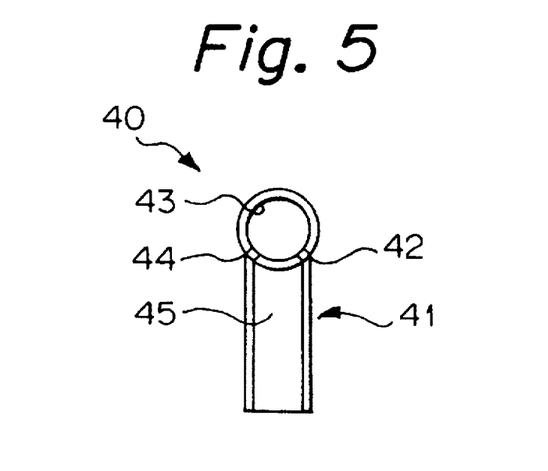
FIG. 5 is an enlarged view of a gas intake means.

The gas intake means 40 includes a plurality of hollow, tubular members provided on the bottom surface of the fermentation tank 2. Preferably, each of the hollow, tubular members is positioned between the drive shafts 31 adjacent relative to one another. One end of each of the hollow, tubular members 41 extends to a circumferential air intake port (not shown). The portion of each of the hollow, tubular members 41 disposed within the fermentation tank includes a head 43, a shoulder 43 and a main body 45. The shoulder 44 is provided with a plurality of gas supply apertures 42 for dispersing gas into the sediment or sludge. The gas supply apertures 42 are oriented toward the bottom surface of the fermentation tank, as shown in FIG. 5. Thus, ejection of gas from the gas supply apertures 42 causes the sediment or sludge to be moved upwardly from the bottom of the fermentation tank.

Figure 6:
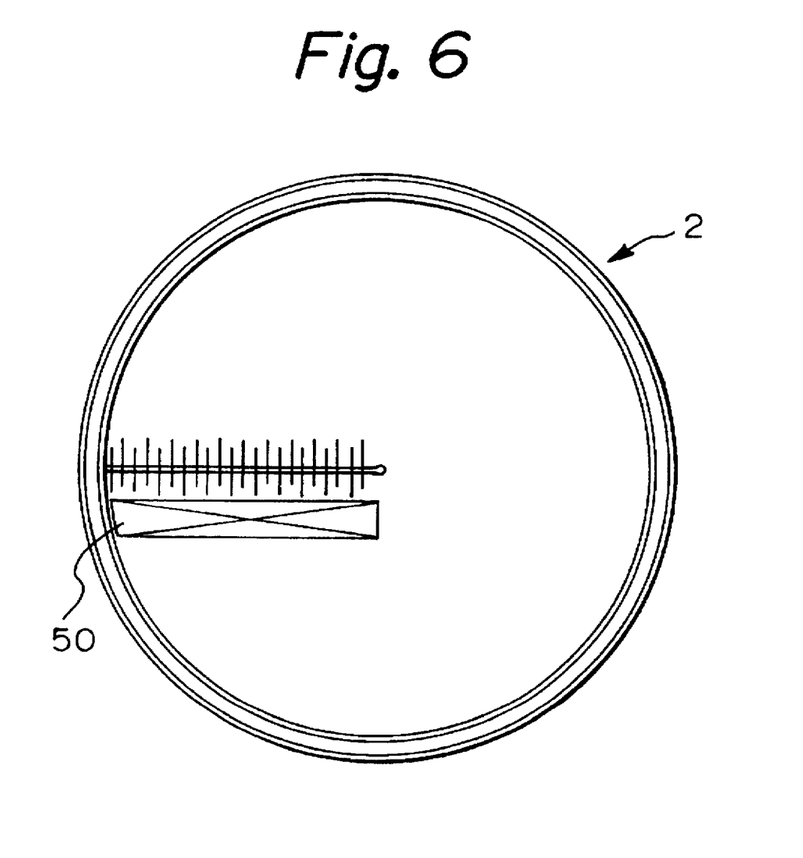
FIG. 6 is a plan view of the fermenter provided with a transfer opening means.
Figure 7:
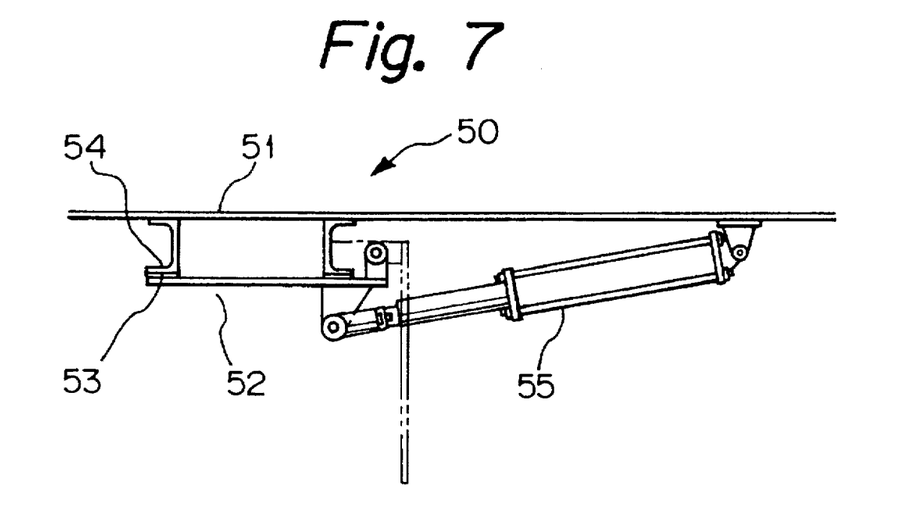
FIG. 7 is a side elevational view, in enlarged scale, illustrating the transfer opening means.

The transfer opening means 50 is illustrated in FIGS. 6 and 7. The transfer opening means 50 includes an opening 51 provided in the bottom surface of the fermentation tank 2, a cover member 52 for openably closing the opening 51, a packing member 53 provided in the circumferential edge of the cover member 52, a block seat 54 to which the packing member 53 is sealingly secured, and a conventional air cylinder 55 provided in the surface opposite to the bottom surface of the fermentation tank 2 for openably closing the cover member 52. The location of the transfer opening means 50 may be changed depending on the particular fermentation tank 2, or, the transfer opening means may be actuated by means of a timer, so that they are opened or closed at a different time. Thus, the sediment or sludge in each stage of the fermentation tank 2 may be transferred to the next stage of fermentation tank.

The filter means 60, in reality, is a deodorizer device provided at the top of the fermentation tank 2, as shown in FIG. 2. The deodorizer device 60 includes a conventional filter member 61, and a deodorizer bed 62 serving as a culture medium to which microorganisms in a stage having changed from thermophilic bacteria to methophilic bacteria are fixed. The microorganisms fixed to the deodorizer bed 62 grow in the presence of odor constituents as a feed, so as to decompose the odor constituents into odor-free state. The compost matured according to the composing method of the above Japanese Patent No. 1829732 is used as a culture medium.

Figure 8:
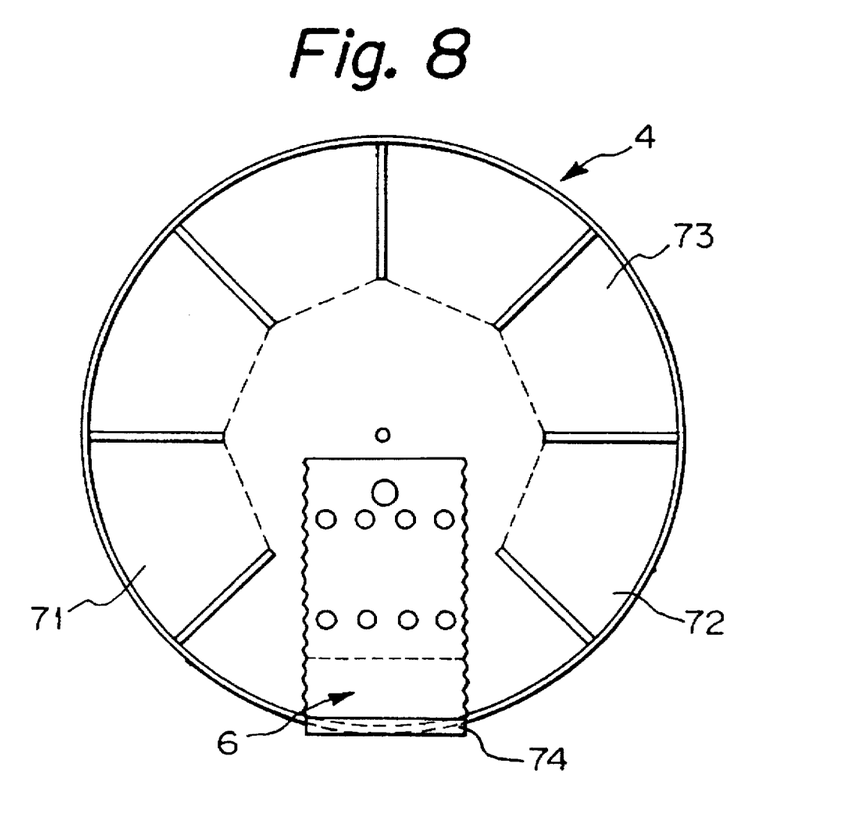
FIG. 8 is a plan view of a maturation tank.

The internal construction of the maturation tank 4 is shown in FIG. 8. The maturation tank 4 also functions as a liquid fermentation tank for causing preliminary fermentation. The maturation tank 4 includes a stock yard 71 for storing therein a moisture conditioner such as sawdust, park or the like, a post-heating yard 72, a stock yard 73 for storing therein sediment after fermentation treatment (product from fermentation process), and a compost output port 5 for discharging the product from fermentation process stored in the maturation tank 4. A liquid fermentation tank 6 for performing preliminary fermentation treatment is also provided below the maturation tank 4.

Figure 9:
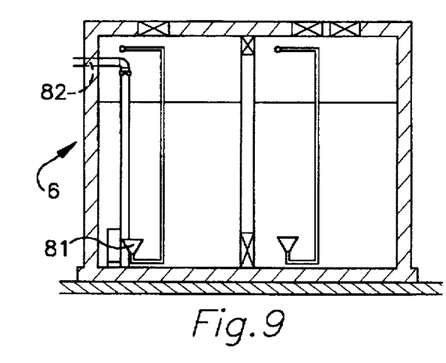
FIG. 9 is a cross-sectional view illustrating a fermentation tank for liquid.
Figure 10:
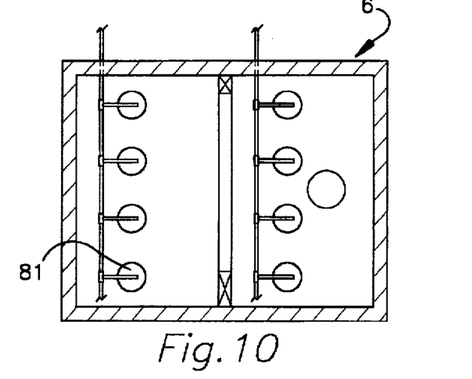
FIG. 10 is a plan view of FIG. 9.

The liquid fermentation tank 6 is shown in FIGS. 9 and 10 its cross-sectional view and plan view, respectively. Two rows of diffusers 81 is provided, each row including 4 (four) diffusers. After completion of preliminary fermentation within the liquid fermentation tank 6, liquid mixture of preliminary fermentation product is transferred upwardly from the liquid fermentation tank 6 into the uppermost stage of fermentation tank 2 by means of a transfer pump 82 in an automatic and constant manner. Moisture conditioning for organic sludge or the like to be fermented is performed by transferring, in a constant rate, the moisture conditioner stored in the stock yard 71 to the uppermost stage of fermentation tank 2 by means of a screw conveyor to be agitated and mixed with the preliminary fermentation liquid mixture.

One experiment in which a sample of excrement was subjected to a fermentation treatment utilizing the multistage, multi-purpose fermentation apparatus according to the invention will be explained below.

(1) Preliminary Fermentation:

A quantity of excrement sample was fed into the liquid fermentation tank 6 at the lowermost stage through an inlet port (not shown) for receiving the material to be treated. The inlet port is directly provided in the liquid fermentation tank 6. The sample was exposed to a forced aeration under a high load condition for three days so as to cause bacteria therein to be grown. Preliminary fermentation has undergone due to the biochemical reaction of the grown bacteria (aerobic bacteria). During this process, temperature of the liquid has increased to 35 to 40 degrees Celsius due to the exothermic phenomenon by means of the growth of the bacteria. This further facilitates the preliminary fermentation. After completion of the preliminary fermentation, a constant volume of the mixed liquid of sample to be treated was transferred, through the transfer pump 82 to the fermentation tank 2 at the uppermost stage.

(2) Fermentation:

A constant volume of the mixed liquid of sample having been transferred from the liquid fermentation tank 6 to the fermentation tank 2 at the uppermost stage was mixed therein with a quantity of moisture conditioner such as sawdust, so as to achieve an apparent moisture content of 60 to 65% and then exposed to a fermentation process. After 45 hours of fermentation, the transfer opening means 50 was automatically actuated so as to cause the cover member 52 to be opened. The mixed liquid of sample having been treated (referred to as "sample sediment" hereinbelow) was transferred to the fermentation tank 2 at the next stage. The thus transferred sample sediment was exposed to a further fermentation process.

The fermentation was facilitated by stirring and mixing a quantity of air supplied from the gas inlet means 40 throughout the sample sediment, by the action of the agitation blades 32 rotating, in the sample, in a plane substantially horizontal to the bottom surface of the fermentation tank 2, and by the action of the arms 21 carrying the drive shafts 31 for the agitation blades 32. During this process, an exothermic phenomenon was caused by reason of the biochemical reaction of bacteria, so that the temperature of the sediment was increased to about 65 degrees Celsius. This further increased the activity of the microorganism, so that the fermentation process was further facilitated.

After 45 hours, the transfer opening means 50 was actuated, so as to transfer the sample sediment into the next fermentation tank 2. During repetition of the above fermentation/transfer processes every 45 hours, the microorganisms in the sample sediment layer were historically developed from thermophilic bacteria (high-temperature bacteria), through methophilic bacteria (medium-temperature bacteria), to cryophilic bacteria (low-temperature bacteria). In accordance with the historical development of the microorganisms, the form of nitrogen (N) contained in the sample sediment was also changed from organic ammonia nitrogen ($N_4$—N) to inorganic nitrate nitrogen ($N_3$—N). Thus, the temperature of the sample sediment approached an ordinary temperature as the sample sediment reached the fermentation tank 2 at the eighth stage. During this process, any surplus water or moisture was evaporated due to the heat caused from exothermic phenomenon of the microorganisms, so that final water content in the sample sediment approached approximately 50%.

(3) Maturation:

The sample sediment, having a moisture content reduced by approximately 50% during the above fermentation process, was then transferred to the maturation tank 4 below the fermentation tank 2 at the lowermost stage, and matured for six weeks. During this period of time, "turn-over" operation was periodically performed. By this means, a quantity of air was supplied to the sediment and thus the temperature of the sediment was decreased. Thus, biochemical reaction of methophilic bacteria and cryophilic bacteria was animated. Accordingly, nitrogen was further changed to nitrate nitrogen, so that stable organic compost could be obtained.

The moisture content of the compost after maturation process was reduced to about 45%. Lignin which is persistent substance was decomposed to quinone substance, i.e., primary humus substance having been changed to genuine humus substance.

In accordance with the vertically oriented, multi-stage, multipurpose fermentation apparatus, it is possible to facilitate effective utilization of a restricted land area, to restrict occurrence of offensive odor or waste water during fermentation process, and to perform all processes including a preliminary fermentation and a maturation process in a sealed apparatus. Thus, the apparatus of the invention is quite suitable for fermentation process in an area adjacent to a large city. The present invention employs a unique agitation means, so that it is not limited to miscellaneous household effluent such as excrement, but it may also be used in various fermentation processes such as food processing for animal meat or fish meat limited to miscellaneous household effluent.

What is claimed is:

1. A vertically oriented, multistage, multipurpose fermentation apparatus comprising:

at least one fermentation tank including a housing of a substantially cylindrical configuration;

a support means extending radially outwardly from a center of said fermentation tank and being rotatable about said center of said fermentation tank;

a plurality of agitation means removably connected to and supported by said support means, each of said agitation means including a plurality of spaced apart agitation blades each of which is rotatable about a central axis of said agitation means extending vertically relative to the bottom surface of said fermentation tank, each of said agitation blades extending from one of said plurality of agitation means in a direction which is horizontal relative to the bottom surface of said fermentation tank such that each of said agitation blades is rotatable only in a plane which is horizontal relative to the bottom surface of said fermentation tank;

a gas intake means disposed above said bottom surface of said fermentation tank and below said agitation means, said gas intake means supplying gas to said fermentation tank;

a transfer opening means disposed in said bottom surface of said fermentation tank and arranged to be opened and closed;

at least one filter means disposed in a top surface of the fermentation tank, said filter means filtering gas being exhausted from the fermentation apparatus; and a maturation tank disposed below said fermentation tank and being in communication with said fermentation tank through said transfer opening means.

2. A vertically oriented, multistage, multipurpose fermentation apparatus according to claim 1, wherein each of said agitation means includes a drive shaft to which said agitation blades are attached, and wherein said drive shaft is removably connected to said support means.

3. A vertically oriented, multistage, multipurpose fermentation apparatus according to claim 1 further comprising a plurality of fermentation tanks wherein at least two stages of fermentation tank are disposed above and connected to the maturation tank.

4. A vertically oriented, multistage, multipurpose fermentation apparatus according to claims 1, wherein said filter means includes a quantity of compost as a deodorizing filter medium, said compost having microorganisms fixed, grown and cultured thereon, said microorganisms being changed from thermophilic bacteria to methophilic bacteria.

5. A vertically oriented, multistage, multipurpose fermentation apparatus according to claim 1 further comprising a liquid fermentation tank for performing preliminary fermentation, said liquid fermentation tank being disposed below the maturation tank.

6. A vertically oriented, multistage, multipurpose fermentation apparatus according to claim 5, wherein said liquid fermentation tank is connected with said fermentation tank, and wherein said fermentation apparatus further comprises a transfer means for transferring a preliminarily fermented product from said liquid fermentation tank to said fermentation tank.

* * * * *